(12) United States Patent
Tatsutani et al.

(10) Patent No.: US 8,828,319 B2
(45) Date of Patent: Sep. 9, 2014

(54) SAMPLE RACK TRANSPORT SYSTEM AND SAMPLE RACK TRANSPORT METHOD

(75) Inventors: Hiroo Tatsutani, Kobe (JP); Tomoyuki Asahara, Kobe (JP); Nobuyoshi Yamakawa, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 132 days.

(21) Appl. No.: 13/073,436

(22) Filed: Mar. 28, 2011

(65) Prior Publication Data

US 2011/0244583 A1 Oct. 6, 2011

(30) Foreign Application Priority Data

Mar. 30, 2010 (JP) ................................. 2010-079196

(51) Int. Cl.
*G01N 21/00* (2006.01)
*G01N 35/00* (2006.01)
*G01N 35/04* (2006.01)
*G01N 35/02* (2006.01)

(52) U.S. Cl.
CPC ........ *G01N 35/026* (2013.01); *G01N 35/00871* (2013.01); *G01N 35/04* (2013.01)
USPC .................. 422/65; 422/62; 422/63; 422/64; 422/66; 422/67; 436/43; 436/180

(58) Field of Classification Search
USPC ................. 422/62–67; 436/43, 180
See application file for complete search history.

(56) References Cited

U.S. PATENT DOCUMENTS

| | | | | |
|---|---|---|---|---|
| 2005/0036912 A1* | 2/2005 | Yamakawa et al. | ............. | 422/65 |
| 2005/0036913 A1* | 2/2005 | Yamakawa et al. | ............. | 422/65 |
| 2005/0214166 A1* | 9/2005 | Itoh | ............. | 422/65 |
| 2009/0220379 A1* | 9/2009 | Wakamiya et al. | ............. | 422/65 |

FOREIGN PATENT DOCUMENTS

| | | |
|---|---|---|
| JP | 11-304808 A | 11/1999 |
| JP | 2003-121451 A | 4/2003 |

* cited by examiner

*Primary Examiner* — Jyoti Nagpaul
(74) *Attorney, Agent, or Firm* — Brinks Gilson & Lione

(57) ABSTRACT

A sample rack transport system comprising: a plurality of transport apparatuses which are connected so as to transport a sample rack to a plurality of sample processing apparatuses; and a control apparatus which communicates with the plurality of transport apparatuses and controls the transport of the sample rack by the plurality of transport apparatuses, wherein at least one of the plurality of transport apparatuses includes a transmission switch which is operated by a user to transmit a signal to the control apparatus, and when the transport of the sample rack has stopped due to a trouble which occurred in one of the plurality of transport apparatuses, responsive to an operation of a transmission switch of another transport apparatus, the control apparatus restarts the transport of the sample rack by the plurality of transport apparatuses. Also, a method for transporting a sample rack.

19 Claims, 10 Drawing Sheets

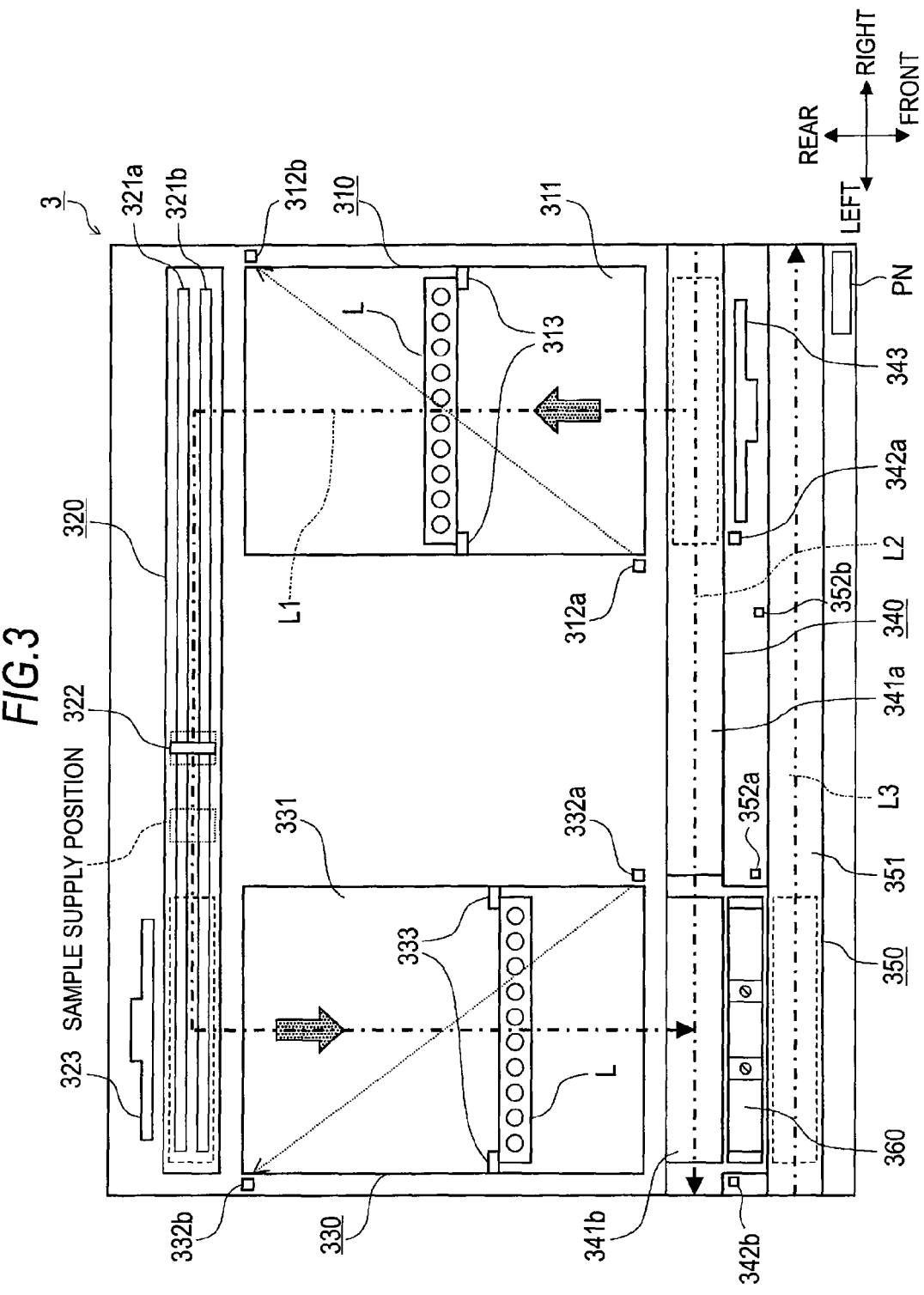

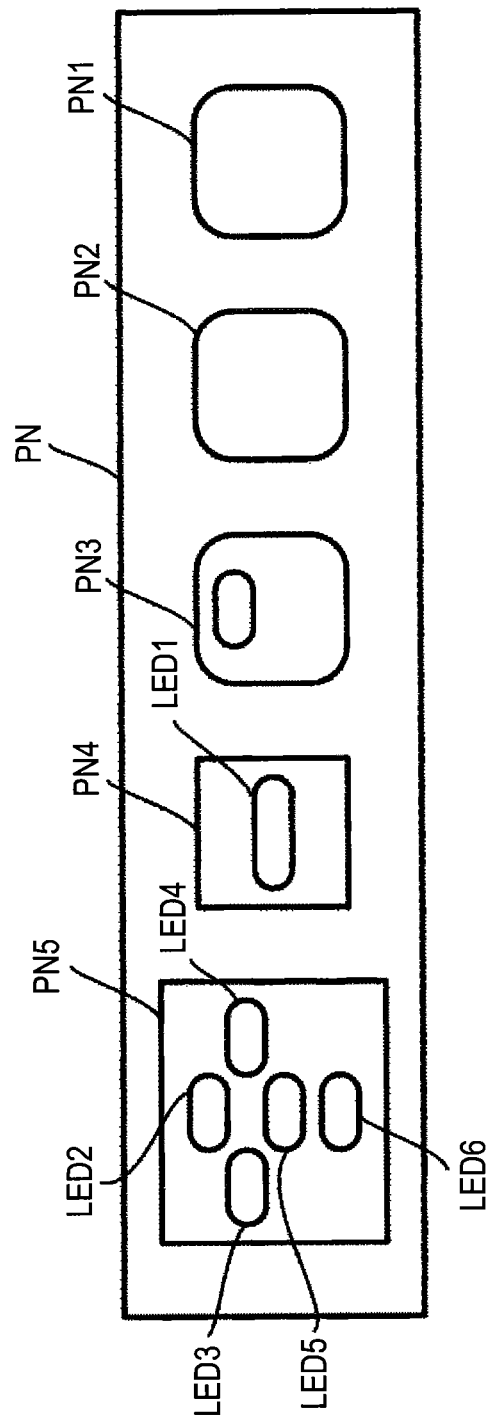

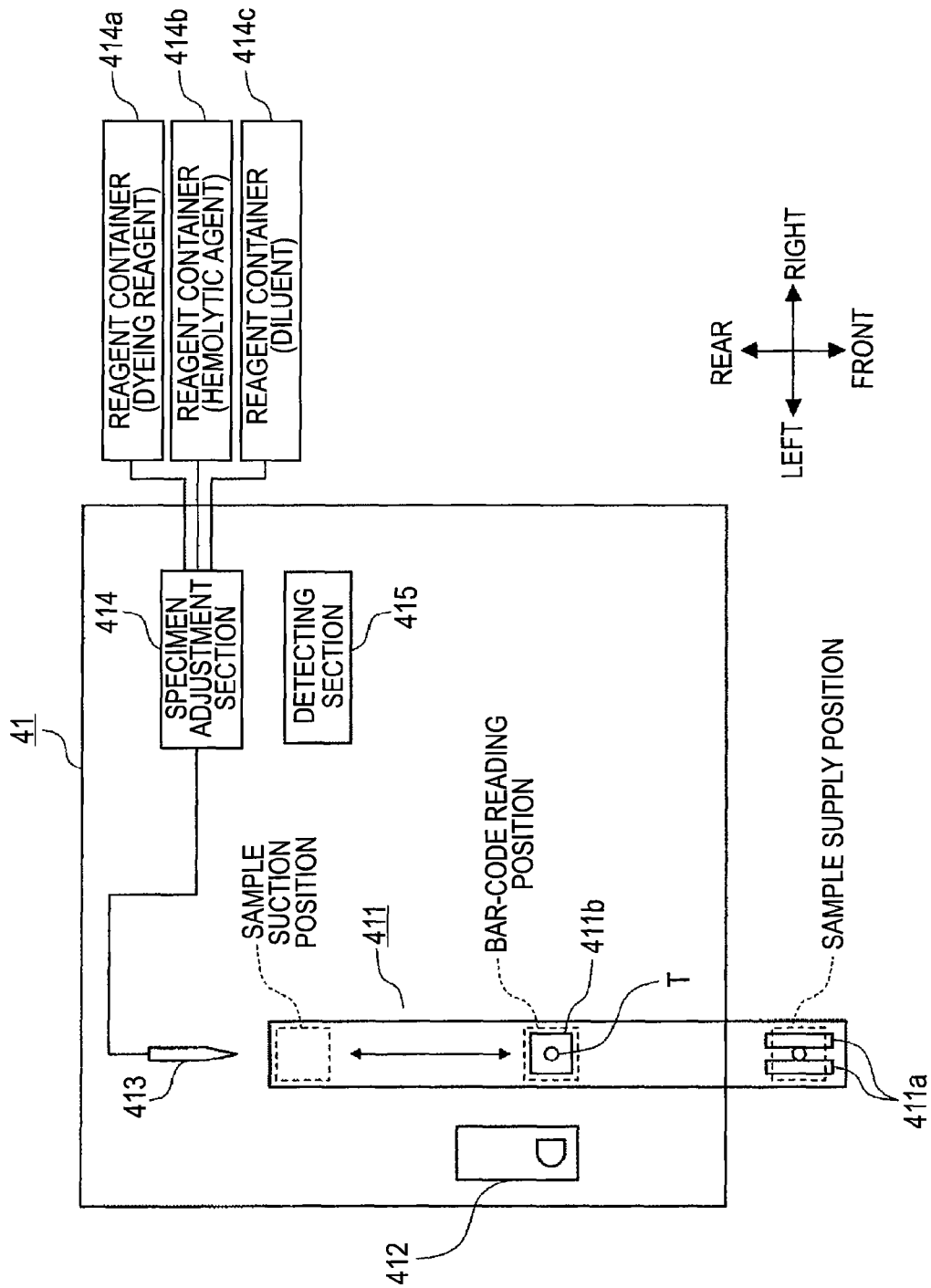

SAMPLE RACK TRANSPORT SYSTEM AND SAMPLE RACK TRANSPORT METHOD

RELATED APPLICATIONS

This application claims priority under 35 U.S.C. §119 to Japanese Patent Application No. 2010-079196 filed on Mar. 30, 2010, the entire content of which is hereby incorporated by reference.

BACKGROUND OF THE INVENTION

1. Field of the Invention

The present invention relates to a sample rack transport system in which a plurality of transport apparatuses transporting sample racks are connected to supply sample racks to a plurality of sample processing apparatuses, and a sample rack transport method.

2. Description of the Related Art

In Japanese Laid-Open Patent Publication No. H11-304808, there is a description of a sample rack transport system including a transport line which transports racks holding samples and can supply the racks to a plurality of processing units, a central control section which controls the transport line and a display section. The transport line is configured by connecting a plurality of transport line units.

In the above-described system, when a situation (hereinafter, error) to be warned of arises, the central control section displays on the display section a warning display screen including a button for clearing a warning, a start-up button for instructing a start of the system, a stop button for instructing a stop of the system and a display area which shows a unit related to the warning.

In the sample rack transport system described in the above-described Japanese Laid-Open Patent Publication No. H11-304808, when an error arises due to a mistake in rack transport in the transport line, a user needs to confirm the transport line unit in which the error arose through the warning display screen displayed on the display section, move up to the transport line unit, remove the rack in which the transport mistake occurred and restart the action of the system by means of the start-up button in the warning display screen.

However, when the above-described configuration is employed in a large-scale sample rack transport system, the distance between the display section for confirming the transport line unit related to the occurrence of the error and the transport line unit in which error arose is large. For this reason, a flow line of the user for confirming the error and restarting the action of the sample rack transport system increases in length.

In order to solve such a problem, providing a button for restarting the action of the system in each transport line unit has been considered.

However, when an error arises due to a rack transport mistake between the adjacent transport line units, the user does not know which transport line unit button should be operated. For this reason, it is necessary to confirm which transport line unit has the error through the warning display screen on the display section. Accordingly, also in the above-described configuration, the flow line of the user for confirming an error and restarting the action of the sample rack transport system increases in length.

SUMMARY OF THE INVENTION

The scope of the present invention is defined solely by the appended claims, and is not affected to any degree by the statements within this summary.

According to a first aspect of the present invention, a sample rack transport system comprising: a plurality of transport apparatuses which are connected so as to transport a sample rack to a plurality of sample processing apparatuses; and a control apparatus which communicates with the plurality of transport apparatuses and controls the transport of the sample rack by the plurality of transport apparatuses, wherein at least one of the plurality of transport apparatuses includes a transmission switch which is operated by a user to transmit a signal to the control apparatus, and when the transport of the sample rack has stopped due to a trouble which occurred in one of the plurality of transport apparatuses, responsive to an operation of a transmission switch of another transport apparatus, the control apparatus restarts the transport of the sample rack by the plurality of transport apparatuses.

According to a second aspect of the present invention, a method for transporting a sample rack to a plurality of sample processing apparatuses by a plurality of transport apparatuses, comprising:

(a) when a trouble occurs in one of the plurality of transport apparatuses after a start of a transport of the sample rack, stopping the transport of the sample rack by the plurality of the transport apparatuses;

(b) when a user operates a switch which is provided in another transport apparatus different from the one transport apparatus, transmitting a signal to a control apparatus from the another transport apparatus; and (c) responsive to the signal transmitted from the another transport apparatus, restarting, by the control apparatus, the transport of the sample rack by the plurality of transport apparatuses.

BRIEF DESCRIPTION OF THE DRAWINGS

FIG. 3 is a plan view showing the configuration of a sample transport unit according to the embodiment.

FIG. 4 is a plan view showing the configuration of an operation panel of the sample transport unit according to the embodiment.

FIG. 6 is a schematic diagram showing the configuration of a measuring unit according to the embodiment.

DETAILED DESCRIPTION OF THE PREFERRED EMBODIMENTS

Figure 1:
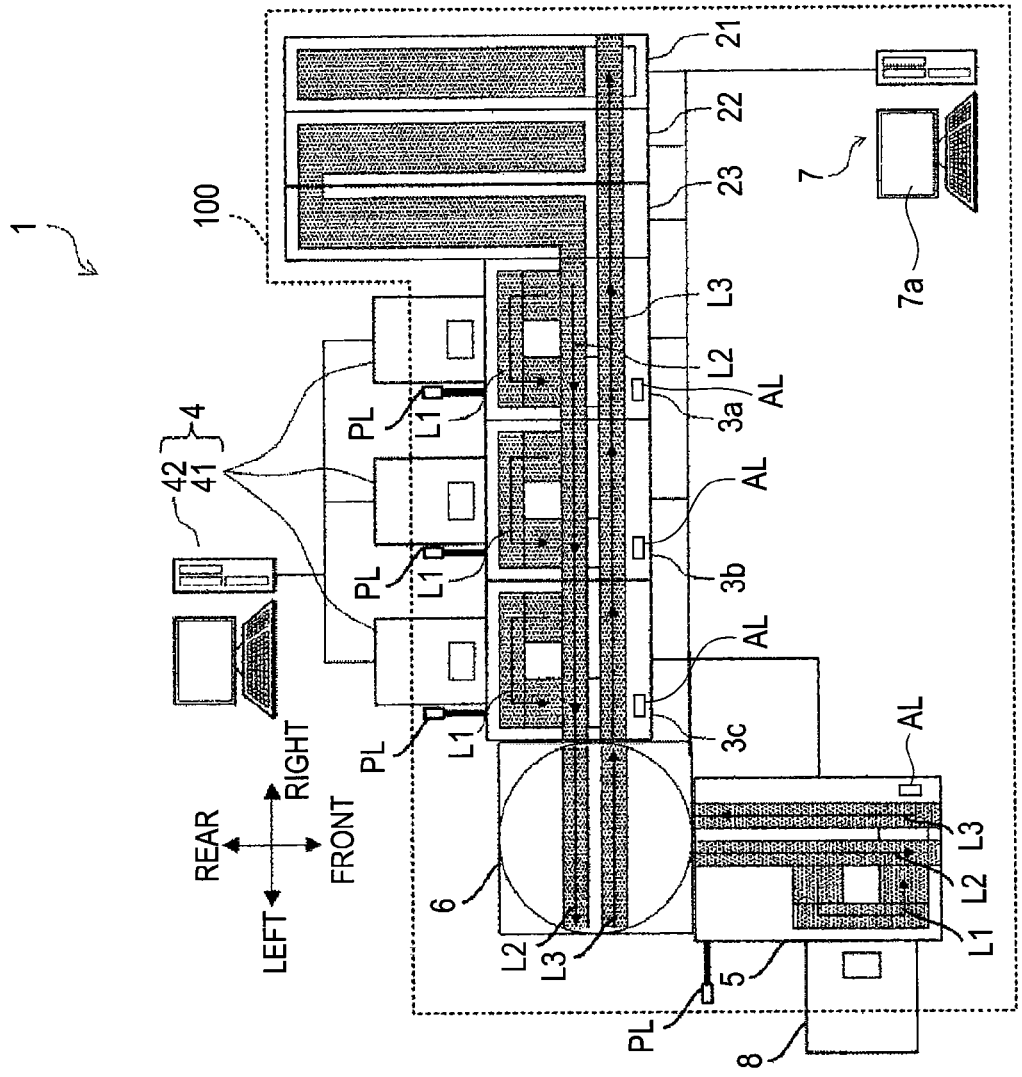
FIG. 1 is a view showing the configuration of a sample analysis system including a sample rack transport system according to an embodiment.

FIG. 1 is a schematic plan view showing the overall configuration of a sample analysis system 1 including a sample rack transport system 100. The sample analysis system 1 according to this embodiment includes the sample rack transport system 100, a blood cell analysis apparatus 4 and a smear preparation apparatus 8. In addition, the sample rack transport system 100 includes a sample recovery unit 21, a sample insertion unit 22, a sample output unit 23, sample transport units 3a, 3b and 3c, a sample transport unit 5, a rotation unit 6 and a transport controller 7.

In addition, in the sample transport units 3a, 3b, 3c and 5, a rotary light PL is provided. When an error arises in the sample transport units 3a, 3b, 3c and 5, the rotary light PL is lit red. Accordingly, a user can recognize error has arisen. In addition, when an error arises in the rotation unit 6, the rotary light PL of the sample transport unit 3c is lit. This will be described later.

In addition, in the sample transport units 3a, 3b, 3c and 5, an alarm AL is provided. When an error arises in the sample transport units 3a, 3b, 3c and 5, the alarm AL is sounded. Accordingly, a user can recognize that an error has arisen. In addition, when an error arises in the rotation unit 6, the alarm AL of the sample transport unit 3c is sounded. This will be described later.

Figure 2A:
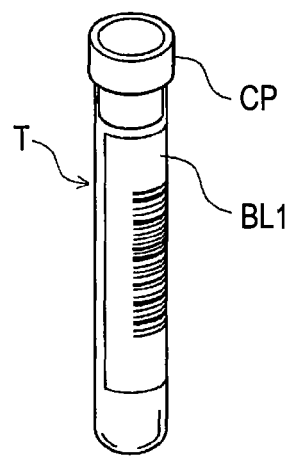
FIGS. 2A and 2B are diagrams showing the configurations of a sample container and a sample rack, respectively.
Figure 2B:
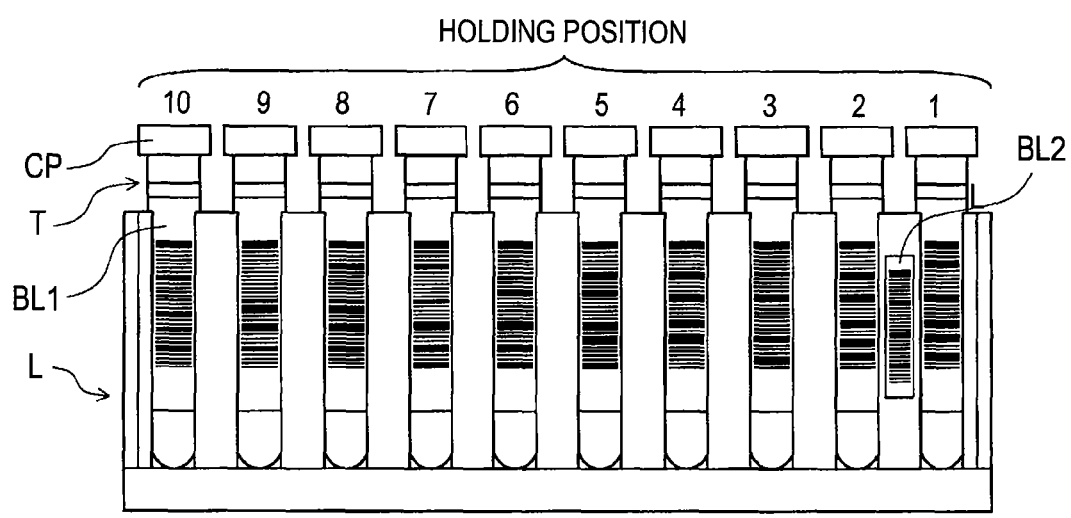

FIG. 2A is a diagram showing the configuration of a sample container T and FIG. 2B is a diagram showing the configuration of a sample rack L. FIG. 2A is a perspective view showing the appearance of the sample container T and FIG. 2B is a front view of the sample rack L.

A sample container T is a tubular container made of glass or a synthetic resin having translucency and the upper end thereof is opened. In the sample container, a blood sample collected from a patient is contained and the opening of the upper end is sealed by a cap section CP. A bar-code label BL1 is adhered to a side surface of the sample container T. A bar-code showing a sample ID is printed on the bar-code label BL1.

In a sample rack L, ten holding positions are formed so as to arrange and hold ten sample containers T in a vertical state (erect state). In addition, as shown in FIG. 2B, a bar-code label BL2 is adhered to the front side of the sample rack L. A bar-code showing a rack ID is printed on the bar-code label BL2.

Returning to FIG. 1, the sample recovery unit 21 stores sample racks L in which analysis has ended. The sample insertion unit 22 stores sample racks L which are inserted by an operator, and outputs the stored sample racks L to the sample output unit 23. In addition, the sample recovery unit 21 and the sample insertion unit 22 are connected to the transport controller 7 so as to communicate therewith.

In the sample output unit 23, a rack ID of the sample rack L which is output from the sample insertion unit 22 and a sample ID of the sample container T which is associated with a holding position in the sample rack L are read. The sample output unit 23 outputs to the sample transport unit 3a the sample rack L, the bar-code of which has been read. In addition, the sample output unit 23 is connected to the transport controller 7 so as to communicate therewith, and the rack ID and the sample ID read by the sample output unit 23 are transmitted to the transport controller 7.

As shown in FIG. 1, each of the sample transport units 3a, 3b and 3c is disposed in front of a measuring unit 41. In addition, the sample transport units 3a, 3b and 3c are connected to each other so that sample racks L can be delivered between the neighboring units. The right end of the sample transport unit 3a is connected to the sample output unit 23 so as to deliver sample racks L. The sample transport units 3a, 3b and 3c are connected to the transport controller 7, respectively, so as to communicate therewith.

As shown in FIG. 1, in the sample transport units 3a, 3b and 3c, two transport lines L1 and L2 for transporting sample racks L are set by dividing cases into the case in which the measurement of a sample is performed in the respective corresponding measuring units 41 and the case in which the measurement is not performed. That is, when the measurement of a sample is performed by the measuring unit 41 or a smear is prepared in the smear preparation apparatus 8, a sample rack L is transported along the transport line L1. When the measurement of a sample is not performed by the measuring unit 41, a sample rack L is transported along the transport line L2 shown by the intermediate left-pointing arrow so as to skip the measuring unit 41.

Further, as shown in FIG. 1, in the sample transport units 3a, 3b and 3c, a transport line L3 for transporting sample racks L to the sample recovery unit 21 is set. That is, a sample rack L, for which measurement or preparation of a smear has ended, is transported along the transport line L3 shown by the front right-pointing arrow and is recovered by the sample recovery unit 21. The configuration of the sample transport units 3a, 3b and 3c will be described later with reference to FIG. 3.

The rotation unit 6 can change the transport direction of sample racks L by 90 degrees. As shown in FIG. 1, the rotation unit 6 does not include a rotary light PL. In addition, the rotation unit 6 does not include an operation panel PN to be described later. The configuration of the rotation unit 6 will be described later with reference to FIG. 5.

The blood cell analysis apparatus 4 is an optical flow cytometry type multiple blood cell analysis apparatus and includes the three measuring units 41 and an information processing apparatus 42. The information processing unit 42 is connected to the three measuring units 41 so as to communicate therewith and controls the actions of the three measuring units 41.

The three measuring units 41 measure a blood sample which is contained in a sample container T. That is, the three measuring units 41 take the sample container T from the sample rack L at a predetermined position on the transport line L1 of the sample transport units 3a, 3b and 3c which are disposed in front of the measuring units, respectively. The blood sample contained in the sample container T is measured in the measuring unit 41. When the measurement in the measuring unit 41 is completed, the sample container T returns to the original holding position in the sample rack L. The configuration of the measuring unit 41 will be described later with reference to FIG. 6.

The sample transport unit 5 is disposed in front of the smear preparation apparatus 8 as shown in FIG. 1. The sample transport unit 5 has a form different from those of the sample transport units 3a, 3b and 3c, but has almost the same configuration, except for a part thereof. In addition, the sample transport unit 5 is connected to the rotation unit 6 so as to deliver sample racks L. The sample transport unit 5 is connected to the transport controller 7 so as to communicate therewith.

As shown in FIG. 1, in the sample transport unit 5, two transport lines L1 and L2 for transporting sample racks L are set by dividing cases into the case in which the preparation of a smear is performed in the smear preparation apparatus 8 and the case in which the preparation of a smear is not performed. When the preparation of a smear is performed in the smear preparation apparatus 8, a sample rack L is transported along the transport line L1. When the preparation of a smear is not performed in the smear preparation apparatus 8, a sample rack L is transported along the transport line L2 shown by the intermediate left-pointing arrow so as to skip the smear preparation apparatus 8.

Further, as shown in FIG. 1, in the sample transport unit 5, a transport line L3 for transporting sample racks L to the former rotation unit 6 is set. That is, a sample rack L, for which measurement or preparation of a smear has ended, is transported to the former rotation unit 6 along the transport line L3 shown by the front right-pointing arrow. The configuration of the sample transport unit 5 is almost the same as those of the sample transport units 3a, 3b and 3c, but a part thereof is different therefrom. Different points in the configuration between the sample transport unit 5 and the sample transport units 3a, 3b and 3c will be described later.

In the smear preparation apparatus 8, a smear of a blood sample is prepared. That is, first, the smear preparation apparatus 8 suctions a blood sample contained in a sample container T at a sample supply position on the transport line L1 of the sample transport unit 5. Next, the suctioned blood sample is dropped onto a glass slide, thinly extended on the glass slide and then is dried. After that, a liquid dye is supplied to the glass slide to dye the blood on the glass slide and a smear is prepared.

Whether the preparation of a smear is required is determined by the transport controller 7 on the basis of the analysis result of the measuring unit 41. As described later, the analysis result of each measuring unit 41 is transmitted to the transport controller 7 via the sample transport units 3a, 3b and 3c. When the transport controller 7 determines that the preparation of a smear is required, the sample rack L storing a target sample is transported along the transport lines L1 of the sample transport units 3a, 3b and 3c corresponding to the smear preparation apparatus 8 and a smear is prepared in the smear preparation apparatus 8.

The transport controller 7 which includes a display section 7a is connected to the sample recovery unit 21, the sample insertion unit 22, the sample output unit 23, the sample transport units 3a, 3b and 3c, the rotation unit 6 and the sample transport unit 5 so as to communicate therewith, monitors the action situation of each unit and controls the driving of each unit. As the transport controller 7, for example, a separate personal computer or a computer incorporated in the system is used.

FIG. 3 is a plan view showing the configuration when the sample transport units 3a, 3b and 3c are viewed from the upper side. Each of the sample transport units 3a, 3b and 3c includes a pre-analysis rack holding section 310, a rack transport section 320, a post-analysis rack holding section 330, rack transport sections 340 and 350 and the operation panel PN. The configurations of the sample transport units 3a, 3b and 3c are the same.

When the measurement of a sample rack L is not performed, the sample rack L is linearly sent to the left end from the right end of the rack transport section 340 along the transport line L2 by belts 341a and 341b of the rack transport section 340.

The sample transport units 3a, 3b and 3c monitor whether a sample rack L is being correctly transported along the transport line L2 by sensors 342a and 342b. On the basis of the detection result of the sample rack L by these sensors, the sample transport units 3a, 3b and 3c determine whether an error occurring due to a mistake in transport of the sample rack L in the rack transport section 340 has arisen.

When the measurement of a sample rack L is performed, the sample rack L is sent to the right end position of the rack transport section 340, which is shown by the broken line in the right lower portion of FIG. 3. That is, the reflective sensor 342a shown in FIG. 3 detects that the sample rack L has been transported to the position shown by the broken line in the right lower portion of FIG. 3. At this timing, the belt 341a is stopped. Then, when a rack pushing mechanism 343 moves backward, the sample rack L is pushed to the front end of a transport passage 311 of the pre-analysis rack holding section 310. When optical sensors 312a and 312b including a light-emitting section and a light-receiving section detect the sample rack L on the transport passage 311, a rack input mechanism 313 moves backward while engaging with the front ends of the sample rack L and the sample rack L is sent to the back. In this manner, when the sample rack L is sent up to the right end position of the rack transport section 320, the belts 321a and 321b are driven and the sample rack L is sent in the left direction.

After that, the sample rack L arrives at the position of a sample container sensor 322. The sample container sensor 322 is a contact sensor. When a detection target sample container T, which is held in the sample rack L, passes through the position immediately under the sample container sensor 322, the contact piece of the sample container sensor 322 is bent by the sample container T and thus the presence of the sample container T is detected.

At a sample supply position positioned on the left side of the position, at which the sample container T has been detected by the sample container sensor 322, by a distance corresponding to two sample containers, a hand section of the measuring unit 41 which will be described later grips the sample container T and takes the sample container T from the sample rack L. The removed sample container T returns to the sample rack L after used in the measurement in the measuring unit 41. While the sample container T returns to the sample rack L, the transport of the sample rack L is on standby.

In this manner, when the measurement of the samples in all of the sample containers T held in the sample rack L is completed, the sample rack L is sent up to the left end position of the rack transport section 320 shown by the broken line in FIG. 3 by the belts 321a and 321b and the driving of the belts 321a and 321b is stopped. Then, the sample rack L is sent to the rear end of a transport passage 331 of the post-analysis rack holding section 330 by a rack pushing mechanism 323. When optical sensors 332a and 332b including a light-emitting section and a light-receiving section detect the sample rack L on the transport passage 331, a rack input mechanism 333 moves forward while engaging with the rear ends of the sample rack L and the sample rack L is sent to the front. At this time, a partition section 360 which is in front of the post-analysis rack holding section 330 and is between the rack transport sections 340 and 350 is controlled to be opened and closed and the sample rack L is positioned in either of the rack transport sections 340 or 350.

As a result of the measurement by the measuring unit 41, when it is determined that the smear preparation apparatus 8 on the downstream side needs to prepare smears related to sample containers T which are held in the sample rack L, the sample rack L moves up to the left end position of the rack transport section 340 by the rack input mechanism 333 in a state in which the rack transport sections 340 and 350 are partitioned by the partition section 360. Then, the sample rack L is output to the sample transport unit on the downstream side by the belt 341b of the rack transport section 340.

On the other hand, as a result of the measurement by the measuring unit 41, when it is determined that the smear preparation apparatus 8 on the downstream side does not need to prepare smears related to the sample containers T which are held in the sample rack L, the upper side of the partition section 360 is dropped to be disposed at the same height as the upper side of the belt 341b of the rack transport section 340 and the sample rack L is moved up to the left end position of the rack transport section 350 by the rack input mechanism 333. In this manner, by the rack input mechanism 333, the sample rack L is moved across the rack transport section 340 from the post-analysis rack holding section 330 up to the left end position of the rack transport section 350, which is shown by the broken line in the left lower portion of FIG. 3. Then, the sample rack L is moved in the right direction along the transport line L3 by a belt 351 of the rack transport section 350. In this manner, the sample rack L which is transported along the transport line L3 is transported to the sample transport unit or the sample recovery unit 21 on the upstream side.

At this time, the sample transport units 3 monitor whether the sample rack L is being correctly transported along the transport line L3 by sensors 352a and 352b. On the basis of the detection result of the sample rack L by these sensors, the sample transport units 3a, 3b and 3c determine whether an error occurring due to a mistake in transport of the sample rack L in the rack transport section 350 has arisen.

FIG. 4 is a plan view showing the configuration of the operation panel PN. As shown in FIG. 4, the operation panel PN includes a start/stop key PN1, an alarm reset key PN2, a measurement mode switching key PN3, a state display section PN4 and a state display section PN5. Hereinafter, the operation panel PN provided in the sample transport unit 3c will be exemplified and described. However, it is the same as the operation panels PN provided in the sample transport units 3a and 3b.

The start/stop key PN1 is a key for inputting an instruction for restarting or stopping the action of the sample transport unit 3c. For example, when an error arises due to a transport mistake, the sample transport unit 3c stops the action of transporting the sample rack L and automatically notifies the transport controller 7 of the occurrence of the error. A user recovers the sample rack L in which the transport mistake has occurred and then depresses the start/stop key PN1. When the start/stop key PN1 is depressed, the sample transport unit 3c transmits to the transport controller 7 depression information showing that the start/stop key PN1 has been depressed.

The alarm reset key PN2 is a key for releasing the sounding alarm AL. When an error arises in the sample transport unit 3c, the sample transport unit 3c sounds the alarm AL to notify a user of the occurrence of the error. The user stops the sounding of the alarm AL by depressing the alarm reset key PN2.

The measurement mode switching key PN3 is a key for switching whether to independently operate the sample transport unit 3c and the measurement unit 41 connected to the sample transport unit 3c, or to connect them to another sample transport unit so as to be operated as the unit constituting the sample rack transport system 100.

The state display section PN4 includes an LED 1 showing whether an error has arisen in the sample transport unit 3c. When there is no error in the sample transport unit 3c, the LED 1 is lit blue. However, when an error arises in the sample transport unit 3c, the sample transport unit 3c notifies a user of the occurrence of the error by lighting the LED 1 red.

The state display section PN5 includes LEDs 2, 3, 4, 5 and 6. The LEDs 2, 3, 4, 5 and 6 are turned off when there is no error in the sample transport unit 3c, the sample transport unit 3b on the upstream side and the rotation unit 6 on the downstream side. When an error arises, the sample transport unit 3c notifies a user of the occurrence position of the error by lighting each LED. The lighting of the LED 2 indicates that the error arose in the rack transport section 320, the lighting of the LED 3 indicates that the error arose in the post-analysis rack holding section 330, the lighting of the LED 4 indicates that the error arose in the pre-analysis rack holding section 310, the lighting of the LED 5 indicates that the error arose in the rotation unit 6 on the downstream side, and the lighting of the LED 6 indicates that the error arose in the transport unit 3b on the upstream side.

Returning to FIG. 3, in the sample transport units 3a, 3b and 3c, stepping motors for driving the rack pushing mechanisms 343 and 323, the rack input mechanisms 313 and 333, the belts 321a, 321b, 341a, 341b and 351 and the partition section 360 are arranged, respectively.

Figure 5A:
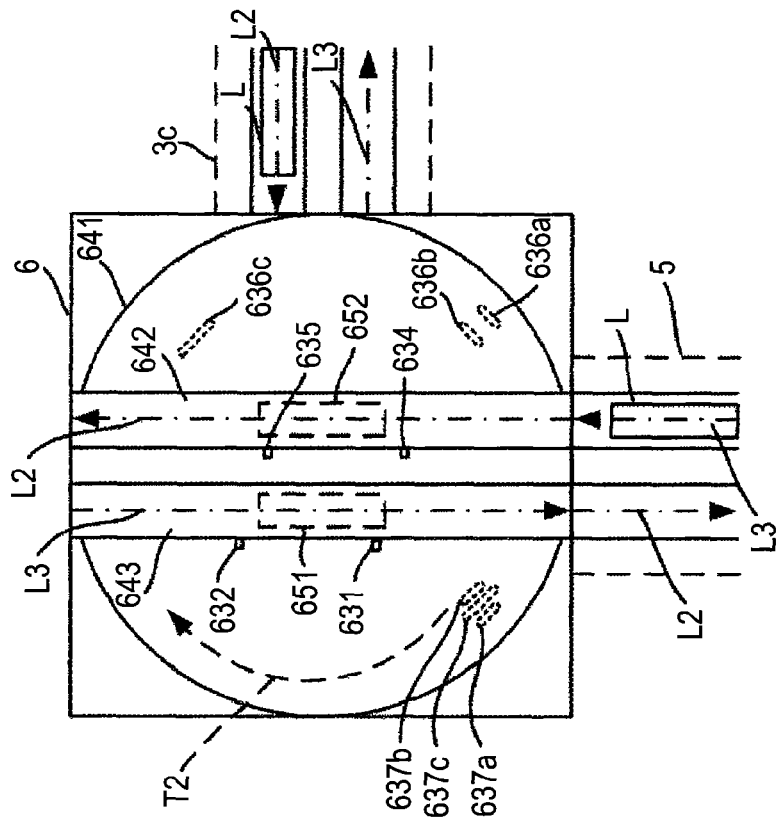
FIGS. 5A and 5B are plan views showing the configuration of a rotation unit according to the embodiment.
Figure 5B:
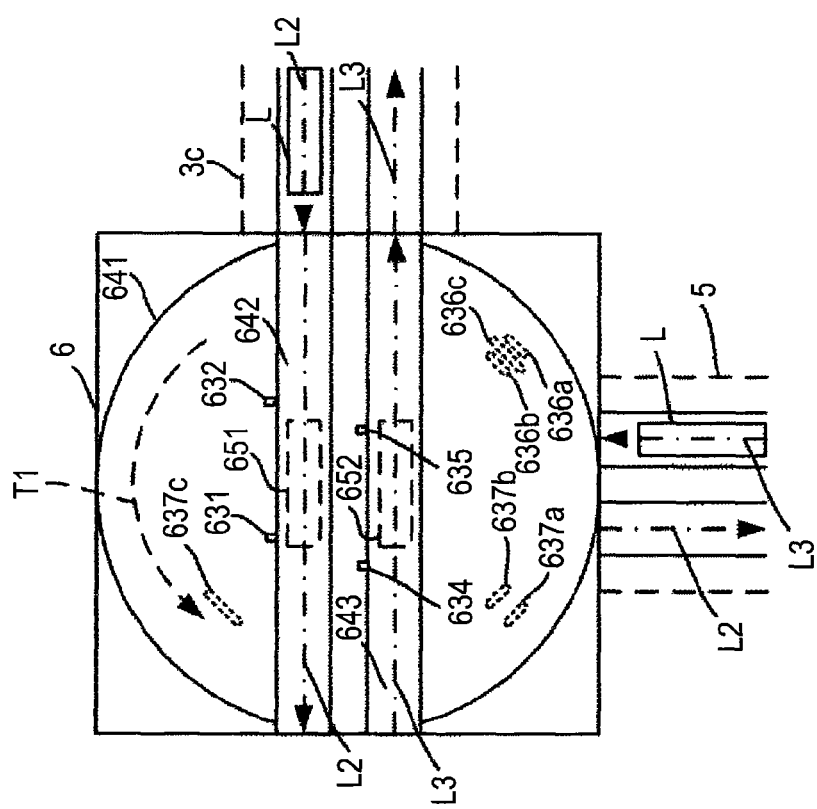

FIGS. 5A and 5B are plan views showing the configuration of the rotation unit 6. As shown in FIGS. 5A and 5B, the rotation unit 6 is connected to the sample transport units 3 and the sample transport unit 5. The rotation unit 6 includes sensors 631, 632, 634, 635, 636a, 636b, 637a and 637b, a turn table 641 and rack transport sections 642 and 643. In addition, in the bottom of the turn table 641, light shielding members 636c and 637c are provided. In addition, in the rack transport sections 642 and 643, rack transport positions 651 and 652 are set.

With reference to FIGS. 5A and 5B, the transport action of the rotation unit 6 will be described by dividing cases into the case in which a sample rack L is discharged from the sample transport unit 3c and the case in which a sample rack L is discharged from the sample transport unit 5.

First, the transport action of the rotation unit 6 when a sample rack L is discharged from the sample transport unit 3c will be described. The sample transport unit 3c transports a sample rack L along the transport line L2, and when moving the sample rack L up to the left end position of the rack transport section 340, the sample transport unit transmits a discharge request to the transport controller 7. When receiving the discharge request, the transport controller 7 transmits a reception instruction to the rotation unit 6.

When receiving the reception instruction, the rotation unit 6 rotates the turn table 641 in a direction T2 by a stepping motor until the light shielding member 636c provided in the bottom of the turn table 641 is detected by the optical sensors 636a and 636b including a light-emitting section and a light-receiving section. When the light shielding member 636c is detected by the sensors 636a and 636b (state shown in FIG. 5A), the rotation unit 6 transmits an introduction request to the transport controller 7.

When receiving the introduction request, the transport controller 7 transmits a discharge instruction to the sample transport unit 3c and transmits an introduction instruction to the rotation unit 6. When receiving the discharge instruction, the sample transport unit 3c discharges the sample rack L to the rotation unit 6 by the rack transport section 340. When receiving the introduction instruction, the rotation unit 6 transports the sample rack L to the rack transport position 651 by a belt of the rack transport section 642. The rotation unit 6 confirms whether the sample rack L has been transported to the rack transport position 651 by detecting the sample rack L with the sensor 632 and then by detecting the sample rack L with the sensor 631. When it is confirmed that the sample rack L has been transported to the rack transport position 651, the rotation unit 6 transmits an introduction completion to the transport controller 7.

When confirming that the sample rack L has been transported to the rack transport position 651, the rotation unit 6 rotates the turn table 641 in a direction T1 by the stepping motor until the light shielding member 637c provided in the bottom of the turn table 641 is detected by the optical sensors 637a and 637b including a light-emitting section and a light-receiving section. When the light shielding member 637c is detected by the sensors 637a and 637b (state shown in FIG. 5B), the rotation unit 6 discharges the sample rack L to the sample transport unit 5 by the rack transport section 642.

Next, the transport action of the rotation unit 6 when a sample rack L is discharged from the sample transport unit 5 will be described. The sample transport unit 5 transports a sample rack L along the transport line L3, and when moving the sample rack L up to the left end position of the rack transport section, the sample transport unit transmits a discharge request to the transport controller 7. When receiving the discharge request, the transport controller 7 transmits a reception instruction to the rotation unit 6.

When receiving the reception instruction, the rotation unit 6 rotates the turn table 641 in the direction T1 by the stepping motor until the light shielding member 637c provided in the bottom of the turn table 641 is detected by the optical sensors 637a and 637b including a light-emitting section and a light-receiving section. When the light shielding member 637c is detected by the sensors 637a and 637b (state shown in FIG. 5B), the rotation unit 6 transmits an introduction request to the transport controller 7.

When receiving the introduction request, the transport controller 7 transmits a discharge instruction to the sample transport unit 5 and transmits an introduction instruction to the rotation unit 6. When receiving the discharge instruction, the sample transport unit 5 discharges the sample rack L to the rotation unit 6 by the rack transport section. When receiving the introduction instruction, the rotation unit 6 transports the sample rack L to the rack transport position 652 by a belt of the rack transport section 643. The rotation unit 6 confirms whether the sample rack L has been transported to the rack transport position 652 by detecting the sample rack L with the sensor 634 and then by detecting the sample rack L with the sensor 635. When it is confirmed that the sample rack L has been transported to the rack transport position 652, the rotation unit 6 transmits an introduction completion to the transport controller 7.

When confirming that the sample rack L has been transported to the rack transport position 652, the rotation unit 6 rotates the turn table 641 in the direction T2 by the stepping motor until the light shielding member 636c provided in the bottom of the turn table 641 is detected by the optical sensors 636a and 636b including a light-emitting section and a light-receiving section. When the light shielding member 636c is detected by the sensors 636a and 636b (state shown in FIG. 5A), the rotation unit 6 discharges the sample rack L to the sample transport unit 3c by the rack transport section 643.

FIG. 6 is a schematic diagram showing the configuration when the measuring unit 41 is viewed from the upper side. The measuring unit 41 includes a sample container transport section 411, a bar-code reading section 412, a sample suction section 413, a specimen adjustment section 414 and a detecting section 415.

The sample container transport section 411 includes a hand section 411a and a sample container setting section 411b. The hand section 411a grips a sample container T positioned at the sample supply position and takes the sample container T from a sample rack L. The removed sample container T is stirred by the hand section 411a and then set in the sample container setting section 411b. The bar-code label BL1 which is adhered to the sample container T set in the sample container setting section 411b is read at the bar-code reading position by the bar-code reading section 412. After that, due to the backward movement of the sample container setting section 411b, the sample container T is positioned at a sample suction position immediately under the sample suction section 413. The sample suction section 413 suctions the sample in the sample container T which is positioned at the sample suction position. Then, the sample container T returns along the original course and returns to the original holding position in the sample rack L.

The specimen adjustment section 414 includes a plurality of reaction chambers. The specimen adjustment section 414 is connected to reagent containers 414a to 414c and can supply the dyeing reagent in the reagent container 414a, the hemolytic agent in the reagent container 414b and the diluent in the reagent container 414c to the reaction chambers. In addition, the specimen adjustment section 414 is also connected to the sample suction section 413 and can supply the blood sample suctioned by the sample suction section 413 to the reaction chambers. Further, the specimen adjustment section 414 mixes and stirs the sample and the reagent in the reaction chamber and prepares a specimen for the measurement by the detecting section 415.

The detecting section 415 measures the specimen prepared by the specimen adjustment section 414. The measurement data obtained by such measurement is analyzed by the information processing unit 42.

Figure 7:
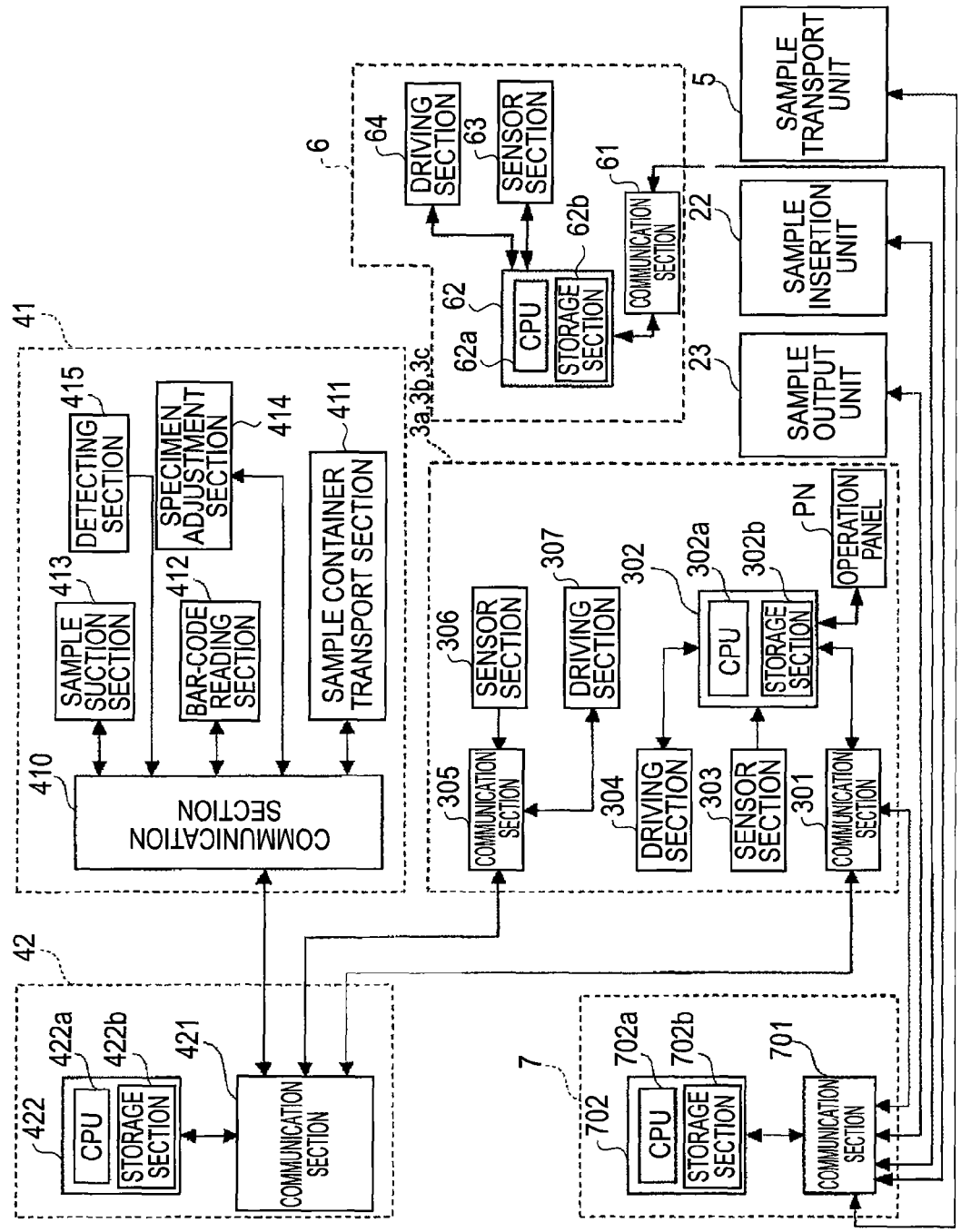
FIG. 7 is a diagram showing the outline of the circuit configurations of the sample transport unit, the rotation unit, the measuring unit, an information processing unit and a transport controller.

FIG. 7 is a diagram showing the outline of the circuit configurations of the sample transport unit 3, the measuring unit 41, the information processing unit 42, the rotation unit 6 and the transport controller 7. In FIG. 7, for the sake of convenience, only one sample transport unit 3 and only one measuring unit 41 are shown. However, the other sample transport units 3 and the other measuring units 41 also have the same configurations.

The sample transport unit 3 includes communication sections 301 and 305, a control section 302, sensor sections 303 and 306 and driving sections 304 and 307. The driving section 307 transports a sample rack L in a section from the pushing of the sample rack L into the pre-analysis rack holding section 301 in FIG. 3 to the pushing to the post-analysis rack holding section 330. The sensors in this section are included in the sensor section 306 and the outputs of these sensors are supplied to the information processing unit 42. The driving section 304 transports a sample rack L in a section other than the transport section of the driving section 307. The sensors in this section are included in the sensor section 303 and the outputs of these sensors are supplied to the transport controller 7.

The communication section 301 performs data communication between the transport controller 7 and the information processing unit 42. The control section 302 includes a CPU 302a and a storage section 302b. The CPU 302a executes a computer program stored in the storage section 302b and controls the driving section 304 in accordance with a CPU 702a of the transport controller 7. The storage section 302b includes storage means such as a ROM and a RAM.

The sensor section 303 includes the above-described sensors 342a, 342b, 352a, 352b, 332a and 332b. The detection signal of the sensor section 303 is output to the control section 302. The driving section 304 includes the above-described rack pushing mechanism 343, rack input mechanism 333, belts 341a, 341b, 351, an elevating mechanism moving the partition section 360 up and down and a stepping motor driving these respective mechanisms.

The communication section 305 performs data communication with the information processing unit 42. The sensor section 306 includes the above-described sensors 312a and 312b and sample container sensor 322 and the detection signal of the sensor section 306 is transmitted to the information processing unit 42 via the communication section 305. The driving section 307 includes the rack pushing mechanism 323, the rack input mechanism 313, the belts 321a and 321b and a stepping motor driving these respective mechanisms. The sections in the driving section 307 are directly controlled by a control section 422 of the information processing unit 42.

When the detection signals of the sensors 312a and 312b in the sensor section 306 are transmitted to the information processing unit 42, the information processing unit 42 transmits the detection signals to the control section 302 via the communication section 301 of the corresponding sample transport unit 3. Therefore, when the CPU 702a of the transport controller 7 inquires the presence or absence of the detection by the sensors 312a and 312b to each sample transport unit 3, the control section 302 of each sample transport unit 3 transmits the presence or absence of the detection by the sensors 312a and 312b to the transport controller 7 on the basis of the detection signals transmitted from the information processing unit 42.

The measuring unit 41 includes a communication section 410, the sample container transport section 411, the bar-code reading section 412, the sample suction section 413, the specimen adjustment section 414 and the detecting section 415. The sections in the measuring unit 41 are directly controlled by the control section 422 of the information processing unit 42.

The information processing unit 42 includes a communication section 421 and the control section 422. In addition, the information processing unit 42 includes an interface for performing image output, an interface for performing input from a keyboard or the like and a reading device such as a CD drive or a DVD drive. However, here, the description thereof will be omitted.

The communication section 421 performs data communication with the communication sections 301 and 305 of the sample transport unit 3 and the communication section 410 of the measuring unit 41. The control section 422 includes a CPU 422a and a storage section 422b. The CPU 422a executes a computer program stored in the storage section 422b. The storage section 422b includes storage means such as a ROM, a RAM and a hard disk.

The CPU 422a performs blood analysis on the basis of the measurement result (particle data) received from the measuring unit 41 and displays the analysis result on the display section. In addition, the CPU 422a transmits the analysis result to the transport controller 7 via the sample transport unit 3.

The sample transport unit 5 has almost the same configuration as that of the sample transport unit 3, but a part thereof is different therefrom. That is, the sample transport unit 5 does not include the communication section 305 of the sample transport unit 3 and the control section of the sample transport unit 5 directly controls the sensor section 306 and the driving section 307 in the sample transport unit 3.

The rotation unit 6 includes a communication section 61, a control section 62, a sensor section 63 and a driving section 64. The rotation unit 6 is not provided with an operation panel PN. A method of coping with the error occurring due to a mistake in rack transport in the rotation unit 6 will be described later.

The communication section 61 performs data communication with the transport controller 7. The control section 62 controls the driving section 64 in accordance with the CPU 702a of the transport controller 7. A storage section 62b includes storage means such as a ROM and a RAM.

The sensor section 63 includes the above-described sensors 631, 632, 633, 634, 636a, 636b, 637a and 637b and the detection signal of the sensor section 63 is output to the control section 62. The driving section 64 includes the turn table 641, the rack transport sections 642 and 643, the rack transport positions 651 and 652 and a stepping motor driving these respective mechanisms.

The transport controller 7 includes a communication section 701 and a control section 702. In addition, the transport controller 7 includes an interface for performing image output, an interface for performing input from a keyboard or the like and a reading device such as a CD drive or a DVD drive.

The communication section 701 performs data communication with the sample insertion unit 22, the sample output unit 23, the sample transport unit 3 and the sample transport unit 5. The control section 702 includes the CPU 702a and a storage section 702b. The CPU 702a executes a computer program stored in the storage section 702b. The storage section 702b includes storage means such as a ROM, a RAM and a hard disk. In accordance with the computer program, the CPU 702a drives and controls the sample insertion unit 22, the sample output unit 23, the sample transport unit 3 and the sample transport unit 5.

In addition, the CPU 702a controls a driving section 226 of the sample insertion unit 22 and a driving section 242 of the sample output unit 23 on the basis of the detection signals from a sensor section 225 of the sample insertion unit 22 and a sensor section 241 of the sample output unit 23. The CPU 702a controls the driving section 304 of the sample transport unit 3 on the basis of the detection signal from the sensor section 303 of the sample transport unit 3. The CPU 702a determines whether the preparation of a smear is required on the basis of the sample analysis result received from the information processing unit 42 via the sample transport unit 3.

Hereinafter, the action of the sample rack transport system 100 when an error occurring due to a transport mistake arises will be described with reference to the flowcharts shown in FIGS. 8 and 9. In this embodiment, the transport mistake means that the transport of a sample rack L is stopped because the sample rack L gets caught or is stuck in the rack transport sections 340 and 350 of the sample transport unit 3 and the rack transport sections 642 and 643 of the rotation unit 6.

Figure 8:
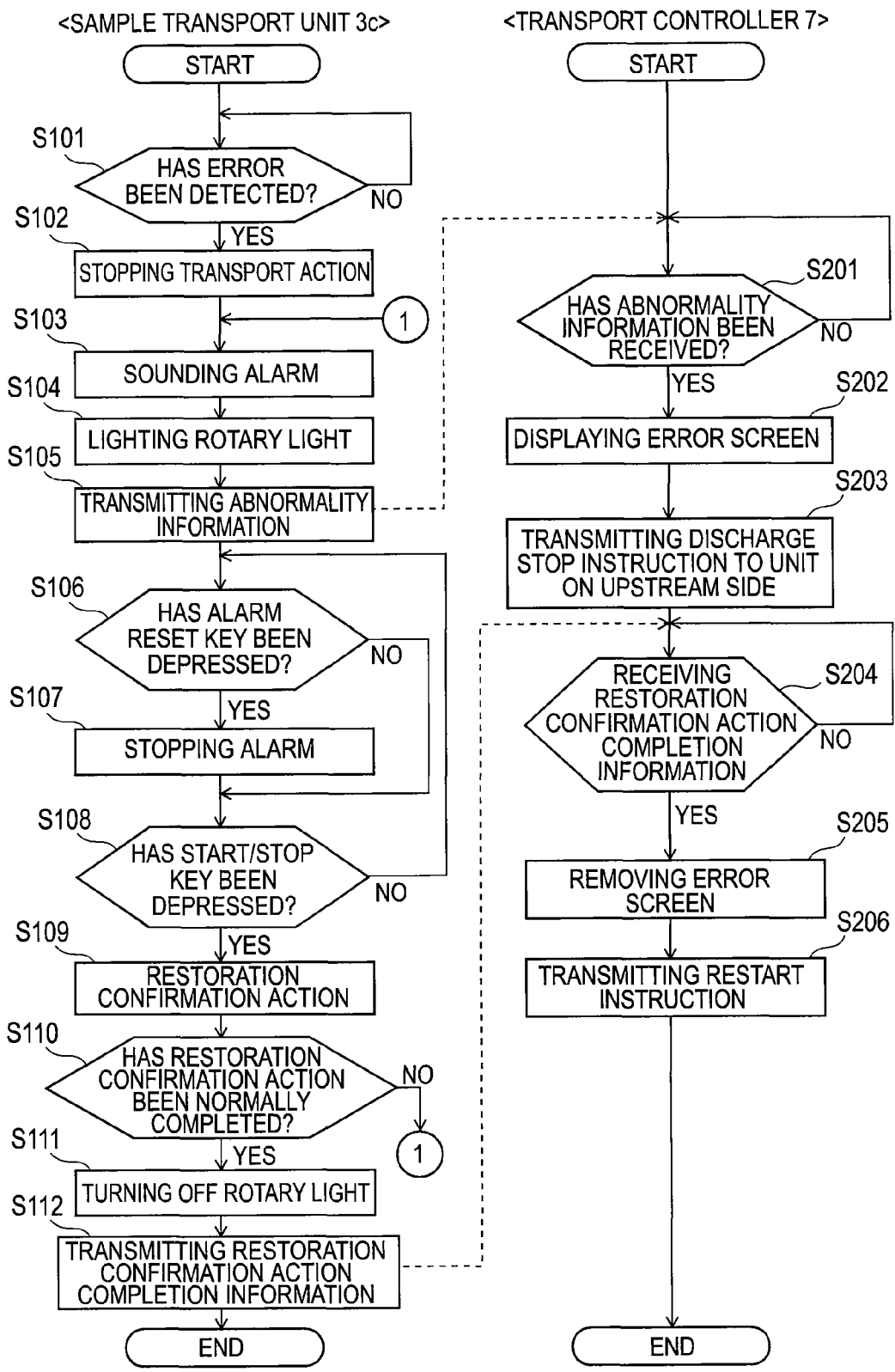
FIG. 8 is a flowchart showing the actions when an error occurring due to a transport mistake arises in the sample rack transport system according to the embodiment.

FIG. 8 is the flowchart showing the actions of the sample transport unit 3c and the transport controller 7 when an error occurring due to a mistake in transport of a sample rack L in the sample transport unit 3c has arisen. Hereinafter, the case in which an error arises in the sample transport unit 3c will be described with reference to the flowchart.

First, the CPU 302a of the sample transport unit 3c determines whether an error occurring due to a transport mistake has been detected in the sample transport unit 3c (S101).

Here, detecting the error occurring due to the transport mistake by the CPU 302a will be described. In the sample transport unit 3c, the sensors 342a, 342b, 352a and 352b are provided. The CPU 302a detects an error occurring due to a transport mistake on the basis of the detection result of these sensors.

For example, in the case in which a sample rack L is transported along the transport line L2, when the sample rack L is detected by the sensor 342a and then is not detected by the sensor 342b within a predetermined time, the CPU 302a determines that the sample rack L is not being correctly transported in the rack transport section 340, that is, an error occurring due to a mistake in transport of the sample rack L has arisen.

In addition, in the case in which a sample rack L is transported along the transport line L3, when the sample rack L is detected by the sensor 352a and then is not detected by the sensor 352b within a predetermined time, the CPU 302a determines that the sample rack L is not being correctly transported in the rack transport section 350, that is, an error occurring due to a mistake in transport of the sample rack L has arisen.

When detecting the error (S101: YES), the CPU 302a stops the action of transporting the sample rack L in the sample transport unit 3c in which the error has arisen (S102), sounds the alarm AL (S103) and lights the rotary light PL (S104). At this time, the CPU 302a lights the LED 1 of the state display section PN4 in a red light.

Next, the CPU 302a transmits to the transport controller 7 abnormality information showing that the error occurring due to the transport mistake has arisen (S105).

Figure 10:
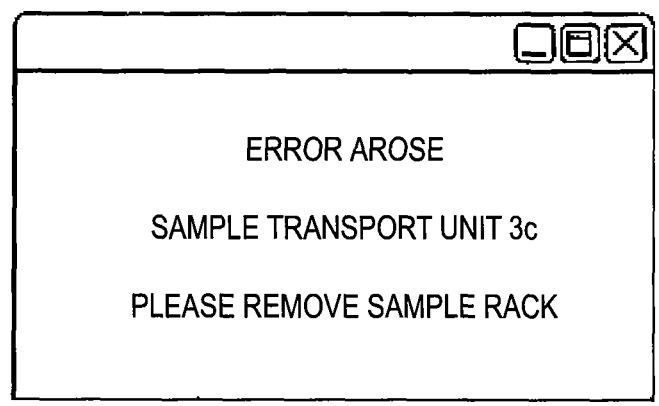
FIG. 10 is an example of an error screen which is displayed in the transport controller when an error occurring due to a transport mistake arises in the sample rack transport system according to the embodiment.

The CPU 702a of the transport controller 7 determines whether the abnormality information has been received (S201), and when determining that the abnormality information has been received (S201: YES), the CPU displays an error screen showing that the abnormality has arisen, which is shown in FIG. 10 (S202). In the error screen, at least information showing the unit in which the error has arisen and a method for removing the error are displayed. Next, the CPU 702a transmits a discharge stop instruction to the sample transport unit 3b connected to the upstream side of the sample transport unit 3c in which the error has arisen (S203). The sample transport unit 3b receiving the discharge stop instruction stops the discharge of the sample rack L to the sample transport unit 3c.

Meanwhile, the CPU 302a determines whether the alarm reset key PN2 has been depressed by a user (S106). When determining that the alarm reset key PN2 has been depressed by the user (S106: YES), the CPU 302a stops the sounding of the alarm AL (S107). When determining that the alarm reset key PN2 has not been depressed (S106: NO) and after the execution of process of S107, the CPU 302a determines whether the start/stop key PN1 has been depressed by the user (S108).

The user removes the sample rack L in which the transport mistake has occurred from the sample transport unit 3c and depresses the start/stop key PN1. The removed sample rack L is inserted again in the sample insertion unit 22 by the user.

When determining that the start/stop key PN1 has been depressed by the user (S108: YES), the CPU 302a transmits depression information showing that the start/stop key PN1 has been depressed to the transport controller 7 and executes a restoration confirmation action in the sample transport unit 3c (S109). Here, an origin seeking action in the rack transport section 340 or 350 is performed as the restoration confirmation action.

Next, the CPU 302a determines whether the restoration confirmation action has been normally completed (S110). Here, the CPU 302a determines whether it was possible to perform the origin seeking in the rack transport section 340 or 350 and whether the sample rack L is not detected by the sensors 342a, 342b, 352a and 352b. When determining that the restoration confirmation action has not been normally completed (S110: NO), the CPU 302a advances the process to S103.

When determining that the restoration confirmation action has been normally completed (S110: YES), the CPU 302a turns off the rotary light PL (S111), transmits restoration confirmation action completion information to the transport controller 7 (S112) and lights the LED 1 of the state display section PN4 in a green light. Therefore, in the sample transport unit 3c, the action of transporting the sample rack L can be executed on the basis of the instruction of the transport controller 7.

Meanwhile, the CPU 702a of the transport controller 7 determines whether the restoration confirmation action completion information has been received (S204), and when determining that the restoration confirmation action completion information has been received (S204: YES), the CPU removes the error screen (S205) and transmits a restart instruction to the whole sample rack transport system 100 (S206). The sample transport unit 3b receiving the restart instruction restarts the stopped discharge of the sample rack L and the sample transport unit 3c receives the sample rack L discharged from the sample transport unit 3b.

As described above, although the actions of the sample transport unit 3c and the transport controller 7 when an error arose in the sample transport unit 3c have been described, the same action as that in the above description can be executed even when the error has arisen in the sample transport unit 3a, 3b or 5. That is, in this embodiment, when an error has arisen in the sample transport unit 3a, 3b or 5, the sample transport unit 3a, 3b or 5 in which the error has arisen and the transport controller 7 can execute the same action as that in the above description.

Figure 9:
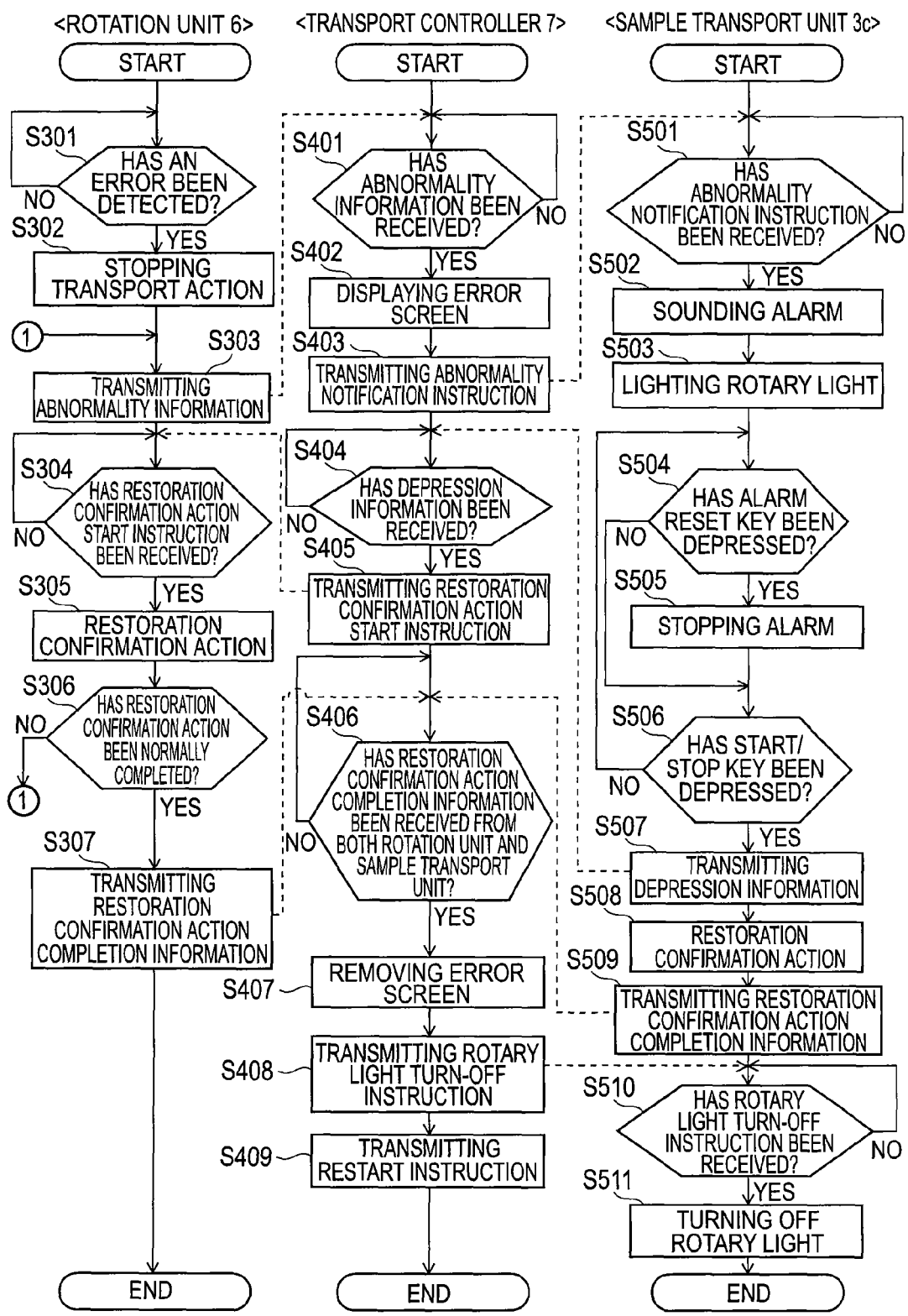
FIG. 9 is a flowchart showing the actions when an error occurring due to a transport mistake arises in the sample rack transport system according to the embodiment.

FIG. 9 is a flowchart showing the actions of the rotation unit 6, the sample transport unit 3c connected to the upstream side of the rotation unit 6 and the transport controller 7 when an error occurring due to a mistake in transport of a sample rack L has arisen in the rotation unit 6. Hereinafter, the actions when an error has arisen in the rotation unit 6 will be exemplified and described with reference to the flowchart shown in FIG. 9.

First, a CPU 62a of the rotation unit 6 determines whether an error occurring due to a mistake in transport of the sample rack L has been detected (S301). Hereinafter, the detection of the transport mistake by the CPU 62a will be described.

For example, in the case in which a sample rack L is transported along the transport line L2, when the sample rack L is not detected by the sensor 632 within a predetermined time after reception of a reception instruction of the sample rack L which is transmitted from the transport controller 7, or when the sample rack L is not detected by the sensor 631 within a predetermined time after detection of the sample rack L by the sensor 632, the CPU 62a detects that a mistake in transport of the sample rack L has arisen. In this case, the CPU 62a determines that the sample rack L is not being correctly transported in the rack transport section 642, that is, determines that the error occurring due to the mistake in transport of the sample rack has arisen.

In addition, in the case in which a sample rack L is transported along the transport line L3, when the sample rack L is not detected by the sensor 634 within a predetermined time after reception of a reception instruction from the transport controller 7, or when the sample rack L is not detected by the sensor 635 within a predetermined time after detection of the sample rack L by the sensor 634, the CPU 62a detects that a mistake in transport of the sample rack L has arisen. In this case, the CPU 62a determines that the sample rack L is not being correctly transported in the rack transport section 643, that is, determines that the error occurring due to the mistake in transport of the sample rack has arisen.

When detecting the error (S301: YES), the CPU 62a stops the action of transporting the sample rack L in the rotation unit 6 in which the error has arisen (S302) and transmits abnormality information to the transport controller 7 (S303).

The CPU 702a of the transport controller 7 determines whether the abnormality information has been received (S401), and when determining that the abnormality information has been received (S401: YES), the CPU displays the error screen (S402) and transmits an abnormality notification instruction to the sample transport unit 3c connected to the upstream side of the rotation unit 6 (S403).

The CPU 302a of the sample transport unit 3c determines whether the abnormality notification instruction has been received (S501), and when determining that the abnormality notification instruction has been received (S501: YES), the CPU sets to standby the discharge of the sample rack to the rotation unit 6, sounds the alarm AL (S502) and lights the rotary light PL (S503). At this time, the CPU 302a lights the LED 5 of the state display section PN5. Therefore, a user knows that the error has arisen in the rotation unit 6 connected to the downstream of the sample transport unit 3c.

Next, the CPU 302a determines whether the alarm reset key PN2 has been depressed by the user, and when determining that the alarm reset key PN2 has been depressed by the user (S504: YES), the CPU 302a stops the sounding of the alarm AL (S505). When determining that the alarm reset key PN2 has not been depressed by the user (S504: NO), the CPU 302a determines whether the start/stop key PN1 has been depressed by the user (S506) after execution of the process of S505.

The user removes the sample rack L in which the transport mistake has occurred from the rotation unit 6 and depresses the start/stop key PN1. The removed sample rack L is inserted again in the sample insertion unit 22 by the user.

When determining that the start/stop key PN1 has been depressed by the user (S506: YES), the CPU 302a transmits depression information (S507) and executes a restoration confirmation action in the sample transport unit 3 (S508). When the restoration confirmation action is normally completed, the CPU 302a transmits restoration confirmation action completion information to the transport controller 7 (S509).

Meanwhile, the CPU 702a of the transport controller 7 determines whether the depression information has been received (S404), and when determining that the depression information has been received (S404: YES), the CPU transmits a restoration confirmation action start instruction to the rotation unit 6 (S405).

Meanwhile, the CPU 62a of the rotation unit 6 determines whether the restoration confirmation action start instruction has been received (S304), and when determining that the restoration confirmation action start instruction has been received (S304: YES), the CPU executes the restoration confirmation action in the rotation unit 6. Here, an origin seeking action of the rack transport section 642 or 643 is executed as the restoration confirmation action.

Next, the CPU 62a determines whether the restoration confirmation action has been normally completed (S306). Here, the CPU 62a determines whether it was possible to perform the origin seeking in the rack transport section 642 or 643 and whether the sample rack L is not detected by the sensor 631, 632, 634 or 635. When determining that the restoration confirmation action has not been normally completed (S306: NO), the CPU 62a advances the process to S303. When determining that the restoration confirmation action has been normally completed (S306: YES), the CPU 62a transmits restoration confirmation action completion information to the transport controller 7 (S307).

Meanwhile, the CPU 702a of the transport controller 7 determines whether the restoration confirmation action completion information has been received from both the rotation unit 6 and the sample transport unit 3c (S406), and when determining that the restoration confirmation action completion information has been received (S406: YES), the CPU removes the error screen (S407), transmits a rotary light turn-off instruction to the sample transport unit 3c (S408) and transmits a restart signal to the whole sample rack transport system 100 (S409). When receiving the restart signal, the sample transport unit 3c restarts the stopped discharge of the sample rack L and the rotation unit 6 executes the action of receiving the sample rack L.

Meanwhile, the CPU 302a of the sample transport unit 3c determines whether the rotary light turn-off instruction has been received (S510), and when determining that the rotary light turn-off instruction has been received, the CPU turns off the rotary light PL (S511) and turns off the LED 5 of the state display section PN5.

An example has been described in which in the sample rack transport system 100 according to this embodiment, when an error arises in the rotation unit 6, the transport of a sample rack is restarted by pressing the start/stop key PN1 of the sample transport unit 3c. However, when an error arises in the rotation unit 6, the transport of a sample rack may be restarted by pressing the start/stop key PN1 of any of the sample transport units 3a, 3b, 3c and 5. In addition, when an error arises in any of the sample transport units 3a, 3b, 3c and 5, the transport of a sample rack may be restarted by pressing the start/stop key PN1 of any of the sample transport units 3a, 3b, 3c and 5 in which there is no error.

As described above, in the sample rack transport system 100 according to this embodiment, a user can recognize the unit related to the error by the alarm AL and the rotary light PL. In addition, in the sample rack transport system 100 according to this embodiment, when an error arises in any of the sample transport units 3a, 3b, 3c and 5 and the rotation unit 6, a user can notify the transport controller 7 of removal of the abnormality and restart the action of transporting the sample rack by removing a sample rack L in which a transport mistake has occurred and depressing the start/stop key PN1 of any of the sample transport units. At this time, a user may depress the start/stop key PN1 of the unit in which the error has arisen or may depress the start/stop key PN1 of the unit in which there is no error. Thus, according to the sample rack transport system 100 according to this embodiment, the flow of a user from the confirmation of the error to the restart of the action can be reduced in length.

The embodiment of the present invention has been described as above. However, the embodiment of the present invention is not limited thereto.

For example, in the above-described embodiment, as an example of the sample processing system, a blood cell analysis system including a plurality of blood cell analysis apparatuses is exemplified. However, the present invention is not limited thereto. For example, the sample analysis system may be a coagulation analysis system including a plurality of blood coagulation analysis apparatuses, a biochemical analysis system including a plurality of biochemical analysis apparatuses or an immune analysis system including a plurality of immune analysis apparatuses. In addition, the sample analysis system may be a urine analysis system including a urine qualitative analysis apparatus and an apparatus for analyzing formed elements in urine.

In the above-described embodiment, when the start/stop key PN1 is depressed, a transport action restart signal may be transmitted to the whole sample rack transport system 100. In this case, the transport controller 7 may be configured to monitor the states of the sample transport units 3a, 3b, 3c and 5 and the rotation unit 6 and to disable the operation of the start/stop key PN1 in the sample transport units 3a, 3b, 3c or 5 until the error is removed.

In the above-described embodiment, the CPU 702a transmits a discharge stop instruction to the unit on the upstream side. However, the present invention is not limited thereto. The discharge stop instruction may be transmitted to the unit on the downstream side. In this case, the unit stops the action of discharging the sample rack L along the transport line L3. In this case, when receiving a restart instruction, the unit on the downstream side may restart the stopped action of discharging the sample rack L.

When an error occurring due to a mistake in transport of the sample rack L arises between the sample transport units adjacent to each other, either of the sample transport unit on the upstream or the downstream side may sound the alarm AL and light the rotary light PL. For example, when an error occurring due to a mistake in transport of the sample rack L arises between the sample transport unit 3a and the sample transport unit 3b, either of the sample transport unit 3a or the sample transport unit 3b may sound the alarm AL and light the rotary light PL.

In the flowchart shown in FIG. 9 of the above-described embodiment, when a user depresses the start/stop key PN1, the CPU 302a transmits depression information and executes a restoration confirmation action in the sample transport unit 3a, 3b, 3c or 5 in which the start/stop key PN1 has been depressed. When the restoration confirmation action is normally completed, the CPU transmits restoration confirmation action completion information to the transport controller 7. However, the present invention is not limited thereto. When an error does not arise in the sample transport unit 3a, 3b, 3c or 5 in which the start/stop key PN1 has been depressed, the CPU 302a may not execute the restoration confirmation action.

Various modifications can be appropriately made in the embodiment of the present invention within the scope of the technical principle shown in the claims.

What is claimed is:

1. A sample rack transport system comprising:
    at least first and second transport apparatuses which are connected so as to transport a sample rack to a plurality of sample processing apparatuses; and
    a control apparatus configured to communicate with the at least first and second transport apparatuses and control the at least first and second transport apparatuses to transport the sample rack,
    wherein the first and second transport apparatuses include first and second transmission switches, respectively, which are operated by a user to transmit signals to the control apparatus, and
    when the transport of the sample rack has stopped due to a trouble which occurred in the first transport apparatus, responsive to an operation of the second transmission switch of the second transport apparatus, the control apparatus controls the at least first and second transport apparatuses to restart the transport of the sample rack.

2. The sample rack transport system according to claim 1, wherein responsive to the operation of the transmission switch of the second transport apparatus, the control apparatus determines whether the trouble in the first transport apparatus has been resolved, and controls the at least first and second transport apparatuses to restart the transport of the sample rack if the trouble in the first transport apparatus has been resolved.

3. The sample rack transport system according to claim 2, wherein responsive to the operation of the transmission switch of the second transport apparatus, the control apparatus transmits to the first transport apparatus an instruction to start a confirmation action for confirming whether the trouble in the first transport apparatus has been resolved,
    the first transport apparatus executes the confirmation action responsive to the instruction to start the confirmation action, and transmits a completion information to the control apparatus when the confirmation action has been completed normally, and
    when the control apparatus has received the completion information, the control apparatus determines that the trouble in the first transport apparatus has been resolved.

4. The sample rack transport system according to claim 1, wherein the at least first and second transport apparatuses include notification sections, respectively, configured to notify an occurrence of the trouble in the first transport apparatus.

5. The sample rack transport system according to claim 4, wherein the notification sections include alarms, respectively, that notify the occurrence of the trouble in the first transport apparatus by sounding.

6. The sample rack transport system according to claim 5, wherein the at least first and second transport apparatuses include stop switches, respectively, configured to stop the sounding of the alarm if an operator operates the stop switches.

7. The sample rack transport system according to claim 4, wherein the notification sections include lights, respectively, that notify the occurrence of the trouble in the first transport apparatus by lighting.

8. The sample rack transport system according to claim 7, wherein the at least first and second transport apparatuses turn off the lights when the trouble in the first transport apparatus has been resolved.

9. The sample rack transport system according to claim 1, wherein the control apparatus includes a display section to display a trouble screen indicating that the first transport apparatus is where the trouble has occurred.

10. The sample rack transport system according to claim 1, further comprising a third transport apparatus,
    wherein the third transport apparatus is a transport apparatus which is not provided with the transmission switch, and when the transport of the sample rack has stopped due to a trouble which occurred in the third transport apparatus, responsive to an operation of the second transmission switch of the second transport apparatus, the control apparatus controls at least the first, second and third transport apparatuses to restart the transport of the sample rack.

11. The sample rack transport system according to claim 10,
    wherein the third transport apparatus is connected so as to be disposed next to any of the first or second transport apparatuses.

12. The sample rack transport system according to claim 11,
    wherein any of the first or second transport apparatuses is connected to an upstream side of the third transport apparatus and includes an alarm that notifies an occurrence of the trouble in the third transport apparatus by sounding and a light that notifies the occurrence of the trouble in the third transport apparatus by lighting, and
    the any of the first or second transport apparatuses is configured not to transport the sample rack to the third transport apparatus, and is configured to sound the alarm and light the light when the trouble has occurred in the third transport apparatus.

13. The sample rack transport system according to claim 12,
    wherein the control apparatus controls the any of the first or second transport apparatuses so as to turn off the light when the trouble in the third transport apparatus has been resolved.

14. The sample rack transport system according to claim 10,
wherein the third transport apparatus is a rack rotation apparatus configured to change a transporting direction of the sample rack to a direction perpendicular to the transporting direction by horizontally rotating the sample rack.

15. A method for transporting a sample rack to a plurality of sample processing apparatuses by at least first and second transport apparatuses, the first and second transport apparatuses including first and second transmission switches, respectively, the method comprising:
(a) when a trouble occurs in the first transport apparatus after a start of a transport of the sample rack, stopping the transport of the sample rack by the at least first and second transport apparatuses;
(b) when a user operates the second transmission switch of the second transport apparatus, transmitting a signal to a control apparatus from the second transport apparatus; and
(c) responsive to the signal transmitted from the second transport apparatus, restarting, by the control apparatus, the transport of the sample rack by the at least first and second transport apparatuses.

16. The method according to claim 15, wherein the step (c) comprises:
(i) responsive to the signal transmitted from the second transport apparatus, determining, by the control apparatus, whether the trouble in the first transport apparatus has been resolved; and
(ii) if the control apparatus determines that the trouble in the first transport apparatus has been resolved, restarting, by the control apparatus, the transport of the sample rack by the at least first and second transport apparatuses.

17. The method according to claim 16, wherein the step (i) comprises:
responsive to the signal transmitted from the second transport apparatus, transmitting to the first transport apparatus an instruction to start a confirmation action for confirming whether the trouble in the first transport apparatus has been resolved;
responsive to the instruction to start the confirmation action, executing the confirmation action by the first transport apparatus;
transmitting a completion information to the control apparatus when the confirmation action has been completed normally; and
determining, by the control apparatus, that the trouble in the first transport apparatus has been resolved when the control apparatus has received the completion information.

18. The method according to claim 15, further comprising when the transport of the sample rack has stopped due to the trouble which occurred in the first transport apparatus, notifying an occurrence of the trouble in the first transport apparatus.

19. The method according to claim 18, further comprising when the trouble in the first transport apparatus has been resolved, stopping the notification.

* * * * *